(12) United States Patent
Taylor et al.

(10) Patent No.: US 8,377,181 B2
(45) Date of Patent: Feb. 19, 2013

(54) ADVANCED PORTABLE OXYGEN CONCENTRATOR

(75) Inventors: Brenton Taylor, Kenwood, CA (US);
Peter Hansen, Santa Barbara, CA (US);
John Stump, Santa Barbara, CA (US);
Patrick Burgess, Dunedin, FL (US)

(73) Assignee: Inogen, Inc., Goleta, CA (US)

( * ) Notice: Subject to any disclaimer, the term of this patent is extended or adjusted under 35 U.S.C. 154(b) by 109 days.

(21) Appl. No.: 13/066,987

(22) Filed: Apr. 29, 2011

(65) Prior Publication Data

US 2012/0167887 A1    Jul. 5, 2012

Related U.S. Application Data

(63) Continuation of application No. 12/930,256, filed on Dec. 30, 2010.

(51) Int. Cl.
*B01D 59/26* (2006.01)

(52) U.S. Cl. ............................................. 96/121; 96/381
(58) Field of Classification Search .................. None
See application file for complete search history.

(56) References Cited

U.S. PATENT DOCUMENTS

| 4,826,510 | A  | * | 5/1989  | McCombs ...................... 96/127 |
| 6,691,702 | B2 | * | 2/2004  | Appel et al. ............. 128/202.26 |
| 6,764,534 | B2 | * | 7/2004  | McCombs et al. ............... 96/111 |
| 6,908,503 | B2 | * | 6/2005  | McCombs et al. ............... 96/130 |
| 7,604,005 | B2 | * | 10/2009 | Jagger et al. ............ 128/202.26 |
| 2009/0277333 | A1 | * | 11/2009 | Sakurai et al. ................... 96/150 |

* cited by examiner

*Primary Examiner* — Fenn Mathew
*Assistant Examiner* — Phillip Shao
(74) *Attorney, Agent, or Firm* — Mark Rodgers (57) ABSTRACT

A portable oxygen concentrator designed for medical use with a novel housing and internal component design that reduces noise and vibration while increasing durability. The improved design of the portable oxygen concentrator further facilitates easy maintenance and repair over the life of the equipment.

8 Claims, 9 Drawing Sheets

ADVANCED PORTABLE OXYGEN CONCENTRATOR

RELATED APPLICATIONS

This application is a continuation of U.S. application Ser. No. 12/930,256 filed Dec. 30, 2010

FEDERALLY SPONSORED RESEARCH

Not Applicable

SEQUENCE LISTING

Not Applicable

BACKGROUND OF THE INVENTION

The inventions generally relates to oxygen concentrators, and more particularly relates to portable medical oxygen concentrators used by patients as a 24 hour a day source of supplemental oxygen.

Portable oxygen concentrators are becoming an increasingly desirable mode of supplying portable oxygen needs to patients requiring Long Term Oxygen Therapy (LTOT). These portable oxygen concentrators are replacing compressed gas cylinders and liquid oxygen systems, which have been the standard of care for many years. Replacing cylinders and liquid oxygen with a portable oxygen concentrator gives a patient the ability to travel onboard aircraft and avoid the requirement to return home to refill a liquid system or exchange empty cylinders. A particularly useful class of portable oxygen concentrators is designed to be used 24 hours a day, allowing users to move about and to travel for extended periods of time without the inconvenience of managing separate oxygen sources for home and portable use. These portable oxygen concentrators are typically in the range of 0.2 to 20 lbs and produce from 0.3 to 5.0 LPM of oxygen. Most of these portable concentrators are based on Pressure Swing Adsorption (PSA) or Vacuum Pressure Swing Adsorption (VPSA) designs which feed compressed air to selective adsorption beds. In a typical oxygen concentrator, the beds utilize a zeolite adsorbent to selectively adsorb nitrogen, resulting in pressurized, oxygen-rich product gas.

Figure 1:
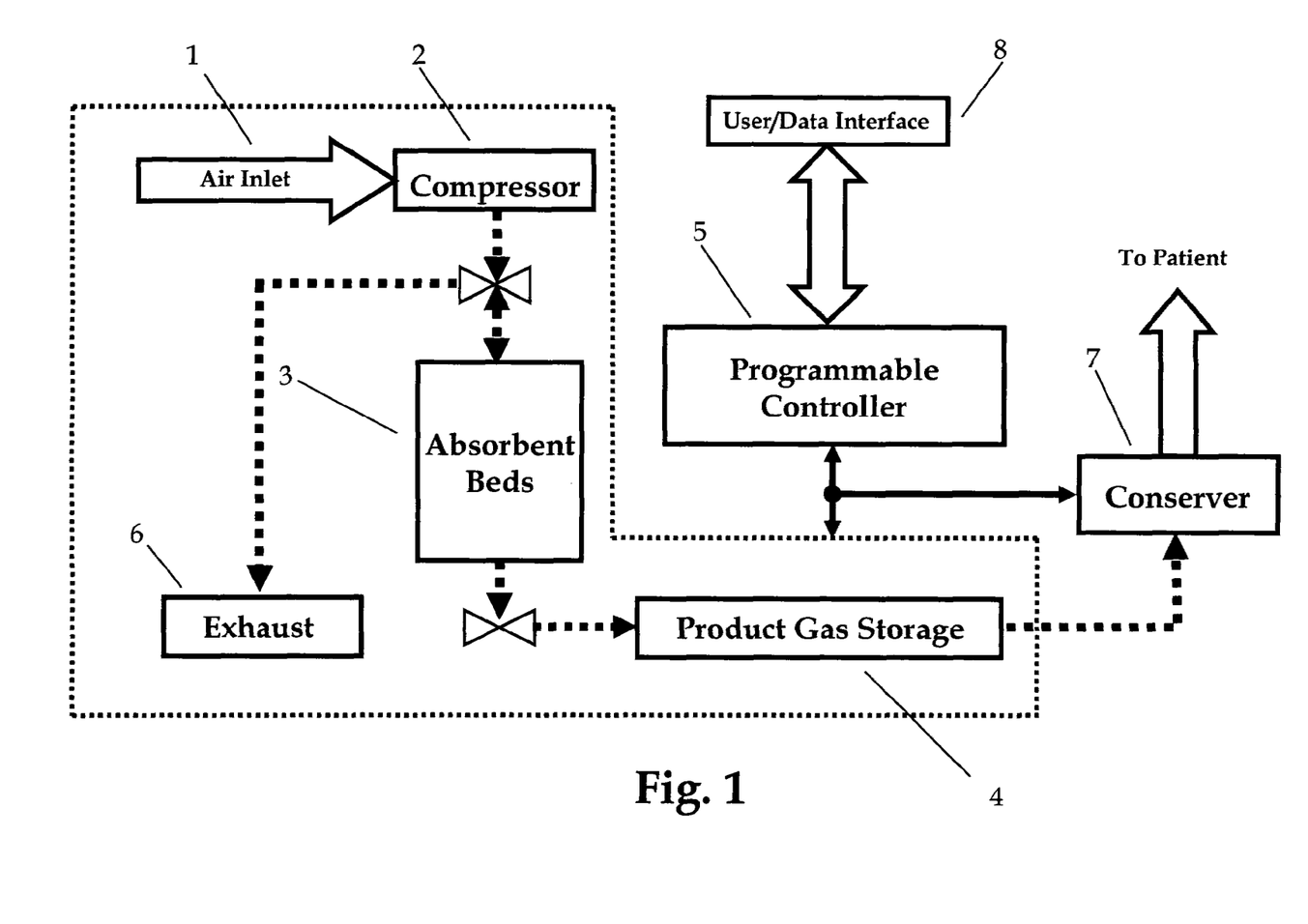
FIG. 1 shows the general elements of gas concentrators as applicable to certain embodiments of the invention.

The main elements in a typical therapeutic oxygen concentrator are shown in FIG. 1. Air is drawn in, and typically filtered, at air inlet 1 before being pressurized by compressor 2 to a pressure of 1.2 to 2.5 atmospheres. The pressurized air is directed by a valve arrangement through adsorbent beds 3. An exemplary adsorbent bed implementation, used in a concentrator design developed by the inventors, is two columns filled with a lithium exchanged zeolite adsorbent in the ratio of about 1 gram of adsorbent per 1-5 ml of oxygen produced. The pressurized air is directed through these absorber vessels or columns in a series of steps which constitute a gas separation cycle, often a PSA cycle or some variation including vacuum instead of, or in conjugation with, compression yielding overall compression ratios of about 1.5:1 to 4.0:1. Although many different arrangements of absorber vessels and gas separation cycles are possible, the result is that nitrogen is removed by the adsorbent material, and the resulting oxygen rich gas is routed to a product gas storage device at 4. Some of the oxygen product gas can be routed back through the bed to flush out (purge) the adsorbed nitrogen to an exhaust 6. Generally multiple adsorbent beds, or columns in the exemplary device, are used so at least one bed may be used to make product while at least one other bed is being purged, ensuring a continuous flow of product gas. The purged gas is exhausted from the concentrator at the exhaust 6.

Such gas separation systems are known in the art, and it is appreciated that the gas flow control through the compressor and the adsorbent beds is complex and requires precise timing and control of parameters such as pressure, flow rate, and temperature to attain the desired oxygen concentration of 80% to 95% purity in the product gas stream. Accordingly, most modern concentrators also have a programmable controller 5, typically a microprocessor, to monitor and control the various operating parameters of the gas separation cycle. In particular, the controller controls the timing and operation of the various valves used to cycle the beds through feed and purge and pressure equalization steps which make up the gas separation cycle. Also present in most portable concentrators is a conserver 7 which acts to ensure that oxygen rich gas is only delivered to a patient during inhalation. Thus, less product gas is delivered than by means of a continuous flow arrangement, thereby allowing for smaller, lighter concentrator designs. A pulse of oxygen rich air, called a bolus, is delivered in response to a detected breath via the conserver. Using a conserver in conjunction with a gas concentrator may reduce the amount of oxygen required to maintain patient oxygen saturation by a factor of about 2:1 to 9:1 A typical concentrator will also contain a user/data interface 8 including elements such as an LCD display, alarm LEDs, audible buzzers, and control buttons. In addition to the above subsystems, most portable oxygen concentrators contain a rechargeable battery and charging system to power the concentrator while away from an AC or DC power source. These battery systems are typically composed of lithium ion cells and can power the concentrator from 2-12 hours depending on the amount oxygen required by the patient and the capacity of the battery pack.

To be practical and usable by an individual needing therapeutic oxygen, portable oxygen concentrators should be less than about 2100 cubic inches and preferably less than 600 cubic inches in total volume, less than about 20 pounds and preferably less than 8 pounds in weight, and produce less than about 45 decibels of audible noise, while retaining the capacity to produce a flow of product gas adequate to provide for a patient's oxygen needs, usually a flow rate prescribed by a medical practitioner in about the range of 1 LPM to 6 LPM. Further, a portable medical oxygen concentrator must work under varied environmental and physical conditions without costly or frequent service or maintenance requirements and should be able to run for upwards of 20,000 hours before major maintenance is required, such as compressor rebuild. Although fixed site PSA based concentrators have been available for many years, such fixed site units may weigh 30-50 pounds or more, be several cubic feet in size, and produce sound levels greater than 45 dBA. Thus portable concentrators involve a significant amount of miniaturization, leading to smaller, more complex designs compared to stationary units, yet they must remain relatively low cost to be available to a wide range of users. System size, weight, and complexity may lead to a necessarily higher degree of integration and design optimization. Moreover, the cost constraints of portable concentrators preclude the use of multiple pressure, temperature, and concentration sensors used by large scale industrial concentrators to help optimize efficiency. Significant teachings in concentrator art exist in just the subject of monitoring and control of various parts of the PSA process. Yet ultra-small portable concentrators have as much or greater need to accomplish such process control. A major required area of innovation in portable concentrator design is the need to accomplish the sort of process control practiced in large scale units without the luxury of the tools available to large scale system designers.

One particular challenge of portable concentrator design is that the devices are typically carried by the user. Since stationary oxygen concentrators are left in one site and the user uses a 50 ft tube extension to move about, the device is not nearly as close to the user under most circumstances. The portable oxygen concentrator must therefore be quieter, create less vibration, and be much more resilient to impacts, and function under constant movement and in various physical orientations.

Therefore, it is necessary to design a portable oxygen concentrator that incorporates an improved mechanical design that mitigates noise and vibration while simultaneously protects the device during impact. Prior art portable oxygen concentrators fail to meet all of these design criteria and as a result, the previously available products did not meet all the needs of the users and the home medical equipment providers. These prior art concentrators failed to meet the users' needs by being too large, too loud, and operated with too much vibration to be near the user 24 hours a day. These prior art concentrators similarly failed the equipment providers due to frequent malfunctions and short service lives. Some prior art portable oxygen concentrators may need a complete compressor rebuild after only 4000 hours, which equates to roughly six months of 24/7 usage. The portable nature of the equipment exposes the devices to being dragged over rough roads, bounced around in the trunks of cars, and knocked off counter tops to impact the ground from several feet. While some prior art equipment might hold up to these high levels of abuse, they do so with added weight and reduced performance parameters such as high noise levels or lowered oxygen flow rates.

Oxygen equipment used for Long Term Oxygen Therapy (LTOT) is optimally deployed for 3-5 years without any service requirements, but when there are service requirements or repairs, they must be able to be performed quickly and inexpensively. Prior art portable oxygen concentrators do not met the objectives of fast and inexpensive repair in the event of damage. Many systems utilize adhesives to permanently bond parts together or have many components integrated into the outer housing such that replacing a damaged housing requires a nearly complete rebuild of the system. Not only do these assembly methods lead to more expensive repairs, but they limit the scope of facilities that can perform the repairs due to requirements for specific tooling and fixturing that common repair facilities would not have access to.

BRIEF SUMMARY OF THE INVENTION

The devices, systems, and methods of this invention each have several aspects, no single one of which is solely responsible for its desirable attributes. Without limiting the scope of this invention, its more prominent features will now be discussed briefly. In one embodiment, the invention provides a portable oxygen concentrator that incorporates novel mechanical design elements to achieve a low noise, low vibration, durable, and easily repaired design. This integrated design approach enables the portable oxygen concentrator of the preferred embodiments to meet the needs of the patients and equipment providers where prior art designs have failed. The novel mechanical design elements include the assembly method of the outer housing components, low volume vibration isolation of the compressor, overlapping housing baffles, and floating column clip assembly system.

Even the inventors' most robust mechanical designs may succumb to the continued abuse of some users, so the inventors designed a novel outer housing assembly system that allows for fast in inexpensive refurbishment of the concentrators so that equipment providers can minimize repair time and cost. In certain preferred embodiments, none of the internal functional components of the housing assembly are anchored to the housing panels, which allows for fast replacement as well as improved vibration and noise isolation.

In a preferred embodiment the housing of the portable oxygen concentrator comprises at least of four panels that snap fit together to form convoluted sound baffles for noise abatement. The outer housing panels preferably snap together with retention clips, and some of these clips may be further secured with fasteners in order to still meet the rigorous durability requirements of this class of device.

In one embodiment, at least two of the panels when assembled form an inlet air plenum, and at least two panels form an outlet air plenum. In a particular aspect, the air plenum is a space between a double-walled section formed by the assembled panels. In one particular embodiment, the side panels wrap around the front and back of the device to mate together forming the inner wall of the double-walled structure. The side panels further have mirror-imaged cut outs to form the inner air vent opening at the front of the device and the inner exhaust vent opening at the rear of the device. To form the outer wall of the intake or exhaust plenum, a convex and stylized end panel is snapped over the mated side panels forming a hollow air plenum. The opening in the end panel is offset from the opening formed in the wall section of the side panels and the air flows through the space formed between the end panels and the wall section of the side panels. The path through both plenums is offset, preferably substantially non-overlapping or completely non-overlapping, to provide noise isolation. A mesh screen may be used on the inlet to keep the airways clear of debris. Between the inlet and outlet plenum there is at least one air barrier, preferably sealed to the housing panels, preferably nonridgidly with foam. An air mover, typically a cooling fan or blower, is carried by the air barrier and provides a forced air path through the barrier. In a preferred embodiment, the air barrier is a printed circuit board. In one as-built embodiment, the adsorbent bed columns are on the inlet side of the air barrier and the compressor is on the outlet side.

In another embodiment, a bottom panel includes a battery mount, and the battery and panels go together such that when the battery is installed, the battery contacts and retains at least two and preferably all of the front, side and rear panels to improve the rigidity of the assembly. The battery is also preferably part of the aesthetic design of the housing.

In another preferred embodiment, the adsorbent columns are carried by a plurality of, preferably two, vibration/shock absorbing mounting elements. These mounting elements may be foam blocks with cutouts, such that the columns are held by the blocks and do not come into direct with the housing. In a particular embodiment, the foam is molded urethane. Additionally, the concentrator may contain one or more modular clips that locate the absorbers and other components relative to each other between the blocks without making any attachments to the housing components.

In a particular embodiment, the modular clips also mount the air barrier/mover, preferably a circuit board and cooling fan, to form an air dam that allows for unidirectional cooling flow that simultaneously intakes room air for the PSA cycle and exhausts waste nitrogen gas from the system without recirculation. Other elements that may be mounted with the columns in the floating assembly include an air dryer, an oxygen product accumulator, and an oxygen sensor.

In a preferred embodiment, the compressor is mounted to a bracket which is in turn mounted to one or more of the housing panels, preferably a non-exterior housing panel to maintain ease of outer housing replacement. The compressor is mounted to the bracket with shock/vibration isolating elements, which in one embodiment may be overmolded rubberized mounts. The bracket is preferably mounted to the housing with a further set of shock/vibration isolating elements, providing two levels of isolation. In one embodiment, the bracket mounting elements are rubberized feet and in a particular version rubber feet with a durometer of 20 A to 60 A. In one version, the bracket is aluminum. The bracket may additionally mount one or more airflow manifolds. The bracket and the lower housing may also preferably include bump stops to limit compressor and bracket deflection during drop or impact.

In one version of the invention, the compressor intake is routed through the fan ducting to ensure a supply of fresh air is always drawn into the compressor.

In another embodiment, an inlet air filter attaches to the compressor. The filter preferably has a tortuous air path for noise reduction, and further may be mounted with its inlet and outlet at right angles to each other for further noise reduction. Substantially all air connections to and from the filter/compressor assemble are by compliant airflow components, and in a particular embodiment molded compliant airflow components to ensure minimum force is applied to the compressor when it is located in its nominal position.

In another embodiment, the compressor is a two piston unit where the piston inputs are fluidly connected by a low profile compliant member. The compliant member in one version comprises one snap fit and one threaded attachment to the pistons. In various versions, the compliant member may be at least two parts of molded rubber joined together, and the member cross section is in the range of 0.02 to 0.08 square inches.

In another embodiment, the portable oxygen concentrator includes a pressure sensor mount where a compliant bracket mounts the pressure sensor and in turn the bracket is mounted to a circuit card. This has the effect of eliminating the hard mounting of the sensor at its designed attachment points, improving the tolerance of the sensor to false readings due to vibration.

BRIEF DESCRIPTION OF THE DRAWINGS

The understanding of the following detailed description of certain preferred embodiments of the invention will be facilitated by referring to the accompanying figures.

DETAILED DESCRIPTION OF THE INVENTION

Referring to FIG. 1, general features of a portable therapeutic gas concentrator are shown. Typically gas is drawn into the inlet through an inlet filter 1 into a compressor 2. Compressed air is then delivered at a rate of about 3 LPM to 30 LPM (through various filters and other devices) to a gas separation section for selectively adsorbing a component of the gas. The preferred embodiments of the invention, although applicable to a variety of gas concentrator implementations, will be described in detail for the case where the inlet gas is air, and the gas separation section is based on PSA, VA, VPSA or some combination thereof, utilizing adsorbent beds 3 which selectively adsorb nitrogen, producing oxygen rich product.

A variety of gas separation section cycle types and bed arrangements are known in the art, most of which can benefit from the embodiments of the invention. Whatever the details of the gas separation section 3, typically product gas is accumulated in a storage device 4. Storage devices may include a tank in the traditional sense, or may be some other device effective for holding a volume of gas, such as a tube, or some other volume filled with an adsorbent to increase its holding capacity. Many modern concentrators used for therapeutic applications also include a programmable controller 5 to operate the concentrator and provide for user interface 8 and communications. Also typical are gas exhaust 6, and delivery to patient, which often is through a conserver device 7.

Earlier portable oxygen concentrator designs were heavier and typically had an oxygen output of only around 0.1 L/lb of system weight. This low output to weight ratio was largely a result of thicker housing walls and redundant components to aid in sound reduction and vibration isolation. For a system that can be carried by the user by a shoulder strap or backpack system, a higher oxygen output to weight ratio is desired. Embodiments of the current invention increase the oxygen to weight ratio by as much as 30% over prior art concentrators while also achieving lower sound levels and increased durability. By comparison, popular existing systems have much lower oxygen to weight ratios. The Inogen One delivered 0.75 L of oxygen and weighed 9.7 pounds for an output to weight ratio of 0.08 L/lb. The Respironics Everflo in measurements made by the inventors produced 1.05 L of oxygen at 10.2 pounds for an output to weight ratio of 0.10 L/lb. The inventors also tested the AirSep Freestyle and measured 0.45 L of oxygen and weighs 4.3 pounds for an output to weight ratio of 0.10 L/lb. While efforts have been made to achieve greater oxygen output to weight ratios in transportable units such as continuous flow portable concentrators like the SeQual Eclipse, these units have integrated cart handles and wheels so they are not designed for the same purpose as a carried or worn concentrator and are not as likely to experience the same level of abuse as the type of concentrator designed by the inventors. As a portable concentrator shrinks to a size where it can be carried, the likelihood of significant drop and impact is greatly increased. System housing wall thickness may be reduced from 0.050" down to 0.030" or less depending on the flame rating requirements of the selected material. Further, as the volume of the concentrator shrinks from around 1200 cubic inches, the noise, vibration, and heat generating components become ever closer to the housing walls, and inlet vents, and exhaust vents. This volume reduction necessitates improved functionality from noise mitigation and vibration mitigation designs while not allowing for additional size or weight to achieve the noise and vibration reductions. For instance the inventors tested the Invacare XPO2 and measured a high oxygen to weight ratio of 0.12 L/lb producing 0.84 L of oxygen at 7.3 pounds, but observed noise level increases to above 45 dBA as a result. As miniaturization of a portable oxygen concentrator progresses the designers are faced with ever more difficult challenges, and this disclosure details several novel design approaches that offer solutions to weight, noise, and durability requirements.

Figure 2:
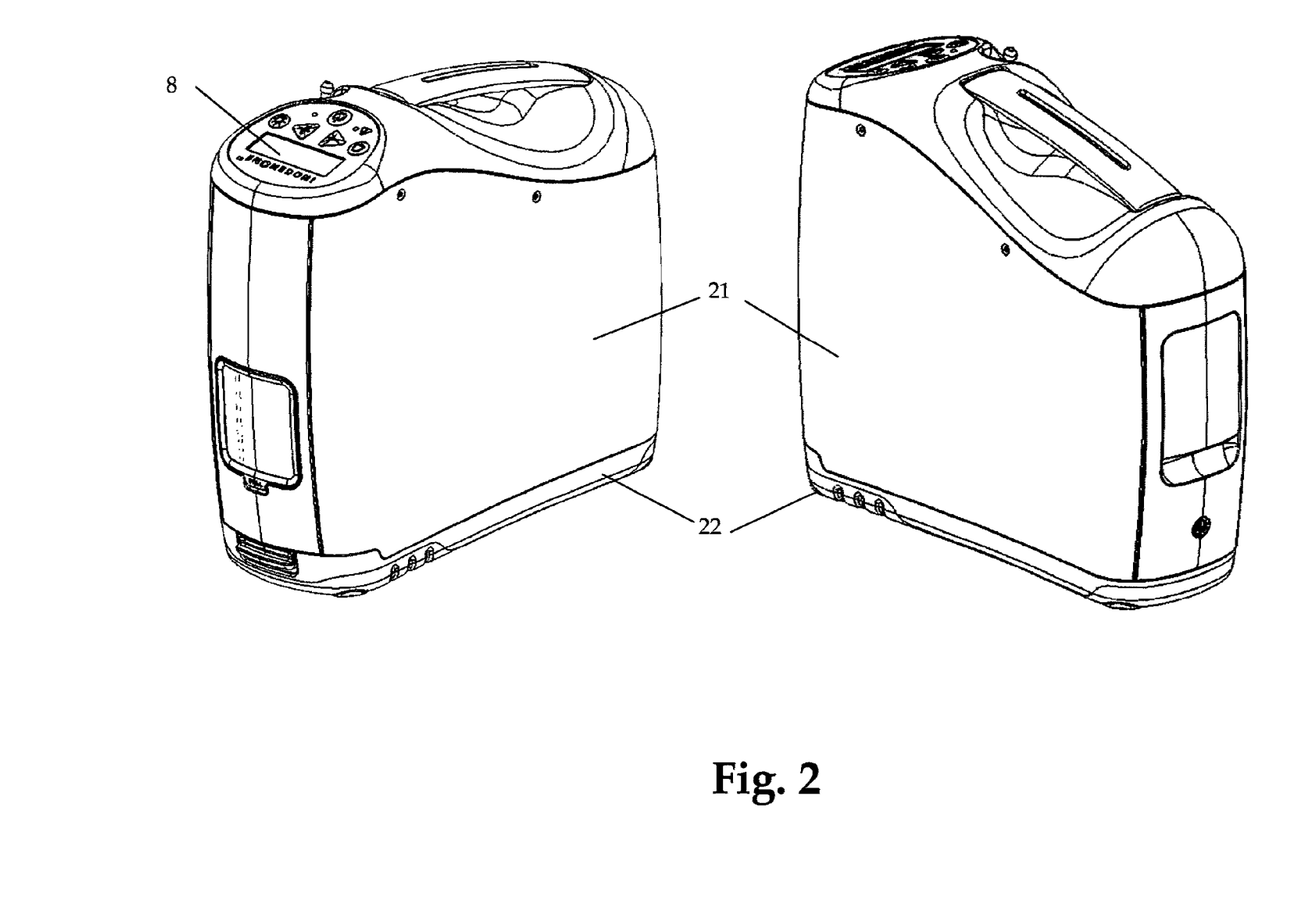
FIG. 2 shows two views of a novel concentrator according to a preferred embodiment.

The Figures depict exemplary implementations that resemble portions of an as-built novel concentrator. However it is to be understood that the details in the Figures are by way of example only and in many cases serve to illustrate a particular version of a novel concept that need not follow the exact configuration of the figures to fall within the teachings and claims of the invention. Referring to FIG. 2 a general illustration of the novel concentrator is shown. Concentrator housing 21, battery 22 and user interface 8 are shown. The battery 22, as depicted in the exemplary figure, forms a nearly seamless integration with the concentrator so that the battery actually forms the bottom of the concentrator and has integral overmolding that functions as an impact absorber and anti-slip footing for the concentrator. Since many drops and impacts would be taken by the bottom of the concentrator, the location of the battery provides a level of protection where damage to the battery would not stop the concentrator from functioning on external power such as AC or DC power. In addition, the sliding rails of the battery and the interlocking components that form the mating rail on the concentrator form a particularly strong and rigid area of the concentrator that allow the battery and shell of the concentrator to dissipate energy without harmfully transmitting it to the working internals of the device. The housing 21 of the concentrator is also devoid of corners and flat surfaces to further stiffen the outer shell, which allows for reduced wall thickness without reduced durability.

Figure 3A:
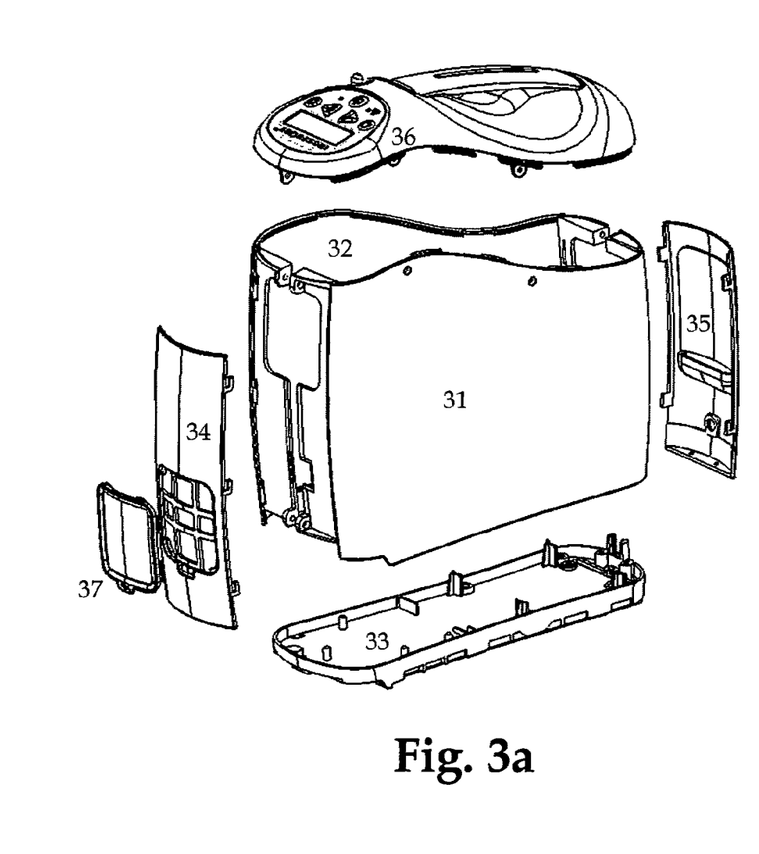
FIG. 3 shows an exemplary outer housing panel arrangement incorporated/in the novel concentrator shown in FIG. 2.
Figure 3B:
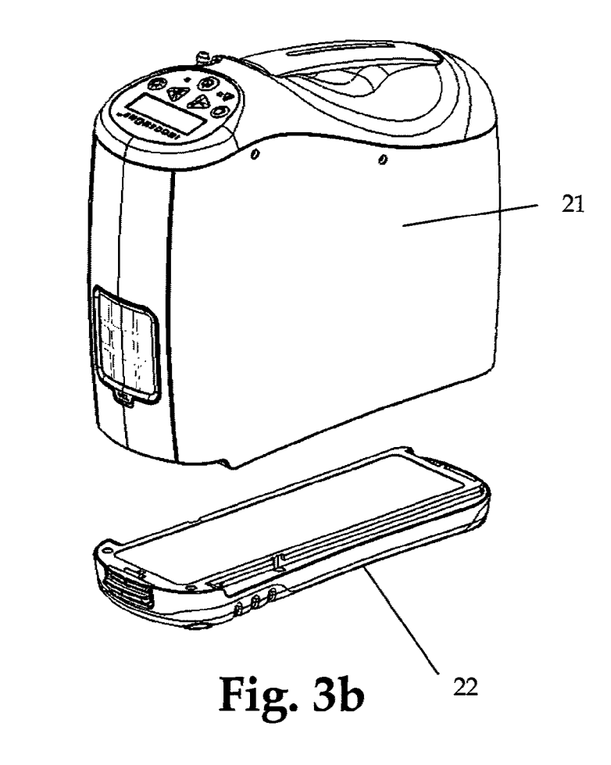

FIGS. 3a and 3b depict a particular embodiment of the concentrator 21. Base panel 33 connects to side panels 31 and 32 as well as front panel 34 and rear panel 35 as can be seen when front and rear panels 34 and 35 are attached they form an air plenum with an offset flow path, which for the exemplary panel design shown is completely non-overlapping. This offset ducting design is a significant improvement for noise isolation. A mesh screen 37 may be employed as a debris filter on the input air plenum. At least some and preferably all the side, front and rear panels are configured to overlap bottom panel 33. When battery 22 is installed, it is configured to contact and retain the panels for added rigidity. Similarly, top panel 35 also contacts all of the body panels as well. In the exemplary implementation, the air plenum space formed by the mating of panels 31, 32 and 34 and the similar air plenum space formed by the mating of panels 31, 32 and 35 create a double walled structure where there are a plurality of connecting points, preferably eight or more. These double walled structures are similar in function to the battery attachment on the bottom of the concentrator where multiple components are mated to increase rigidity and strength while also providing for noise reduction and easy serviceability. In one particular embodiment, the side panels wrap around the front and back of the device to mate together forming the inner wall of the double walled structure and are the two side panels and the top panel are joined with a single screw creating a three point anchor system. The side panels further have mirror imaged cut-outs to form the inner air vent opening at the front of the device and the inner exhaust vent opening at the rear of the device. To form the outer wall of the intake or the exhaust plenum, a convex and stylized panel is installed by engaging retention clips that protrude from the convex outer panel through slots on the side panels. These clips and slots are locked into place when the panel is slid upward and further reinforced because the battery blocks the panel from disengagement in the downward direction. The opening in the end panel is offset from the opening formed in the wall section of the side panels and the air flows through the space formed between the end panels and the wall section of the side panels. The path through both plenums is offset, preferably substantially non-overlapping or completely non-overlapping, to provide noise isolation by eliminating a direct path for noise to exit the device.

Figure 4A:
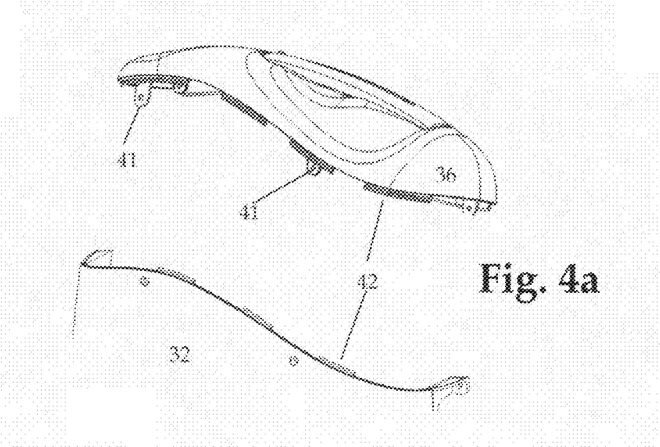
FIG. 4 illustrates the panel snap retention clips and fasteners incorporated in the novel concentrator shown in FIG. 2.
Figure 4B:
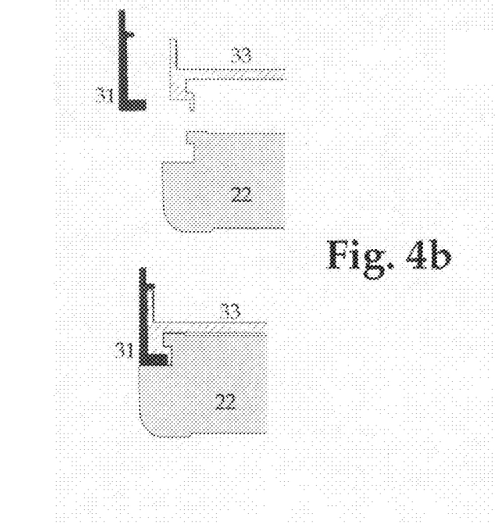
Figure 4C:
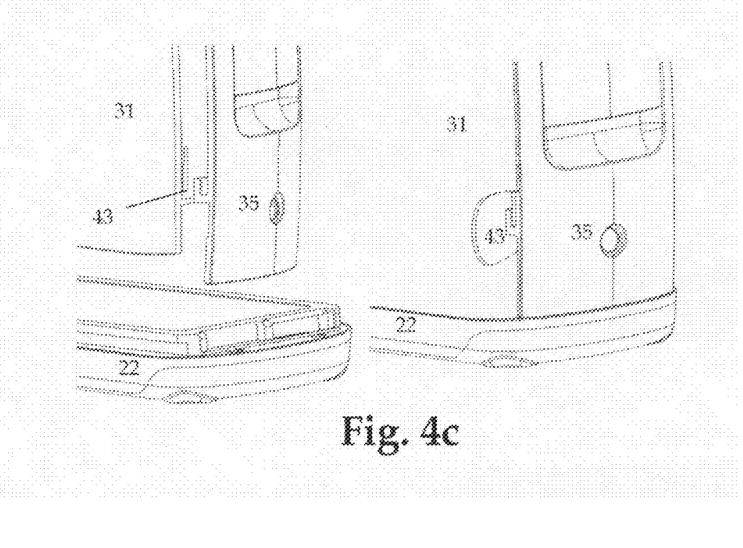
Figure 5:
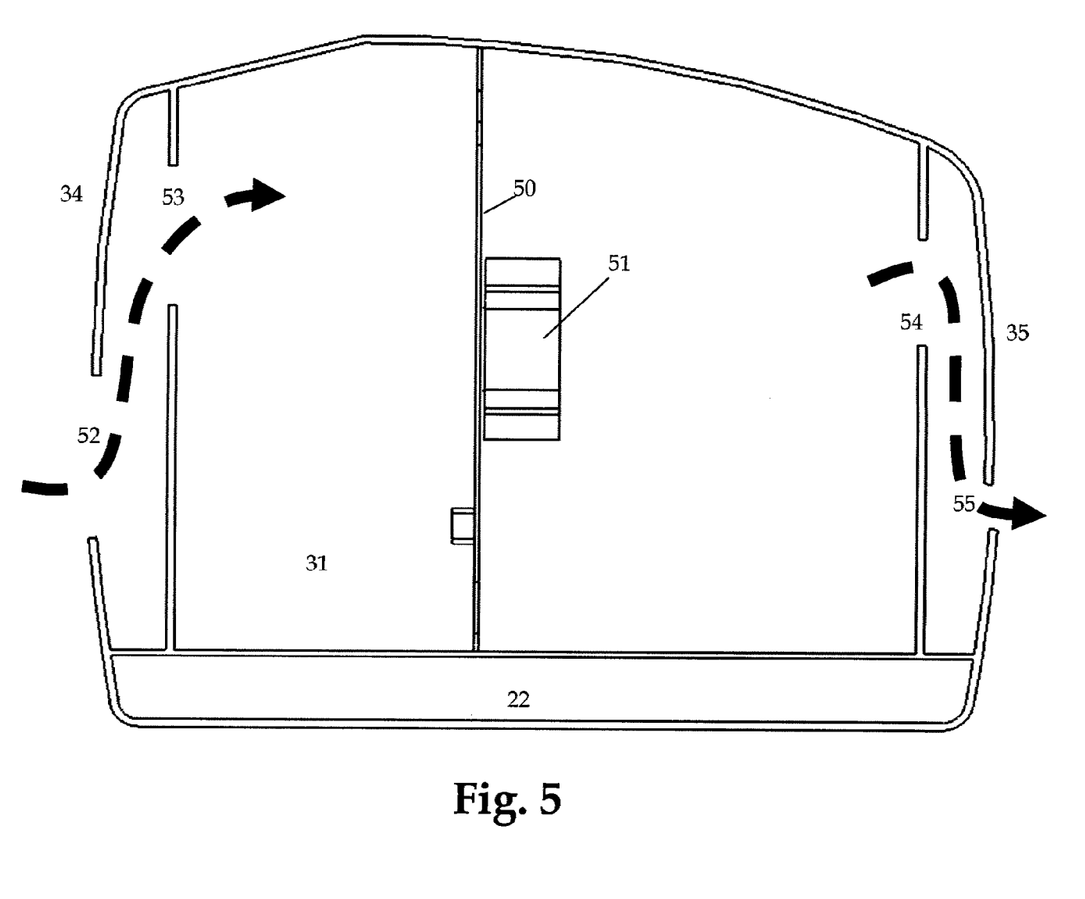
FIG. 5 depicts the air path through the concentrator body, air barrier, and blower incorporated in the novel concentrator shown in FIG. 2.

As shown in FIGS. 4a, b and c panels can be attached to each other via an interference fit such as snapped together with retention clips 42 and 43. When assembled, retention clips may be further reinforced with fastener mounts 41 to ensure that housing holds its shape during impact to prevent undue deformation to internal components. The multitude of snapping features or other forms of interference fit type of fastening devices also allows for a reduction in the number of screws or fasteners required to assemble the concentrator since panels can be locked in place by two fasteners while maintaining strength around the entire perimeter of the panel through the snap features. This assembly method greatly reduces the assembly time and weight that would be required to have a high number of fasteners. For example, the SeQual Eclipse is a simple clamshell design that 10 screws to fasten the two halves together. The inventors design uses 13 screws to fasten six panels together for roughly 50% less fasteners per housing panel. A particular implementation is shown in FIGS. 4b and 4c. As shown in FIG. 4b, when side panel 31 is mated with bottom panel 33, a rail is formed along the length of the panels. When battery 22 is installed, the side panel can no longer be removed because the retention clips must be disengaged in the direction of movement that is blocked by the battery 22. As shown in FIG. 4c, back panel 35 attached to side panels 31 and 32 by sliding upwards to engage the retention clips 43. When battery 22 is installed, back panel 35 is prevented from sliding downward and thus cannot be disengaged by drop or impact. Similar arrangements as shown in the Figures also apply to the front and other side panels. Thus when battery 22 is installed, all four panels are contacted and restrained such that the panels cannot be disassembled with battery in place and structural integrity is greatly increased. Referring to FIG. 5, the plenums formed by the assembled panels are shown. Input 52 is offset from opening 53 as output 55 is offset from opening 54. Preferably an air barrier 50 is present within the housing between the input and output plenums, and it carries an air mover 51, which provides the only airflow path through the barrier. In a particular embodiment barrier 50 has a plurality of functions such as an electronic circuit board and air mover 51 is a cooling fan mounted to the board 50. The circuit board 50 is preferably sealed to the housing with foam to prevent air leakage back across the air barrier. The air flow through the body is shown. In a particular as built embodiment, the absorber columns are in the input side of the barrier and the compressor is in the output side of the barrier. When assembled the panels and barrier constitute a very rigid shell with controlled noise airflow that is particularly suited to an oxygen concentrator where room air must be drawn into the system as a source of oxygen and the nitrogen rich exhaust gas must be expelled from the concentrator. It is advantageous to separate these gas streams so that there is no excess nitrogen drawn into the air inlet of the compressor.

Figures 6A, 6B, 6C:
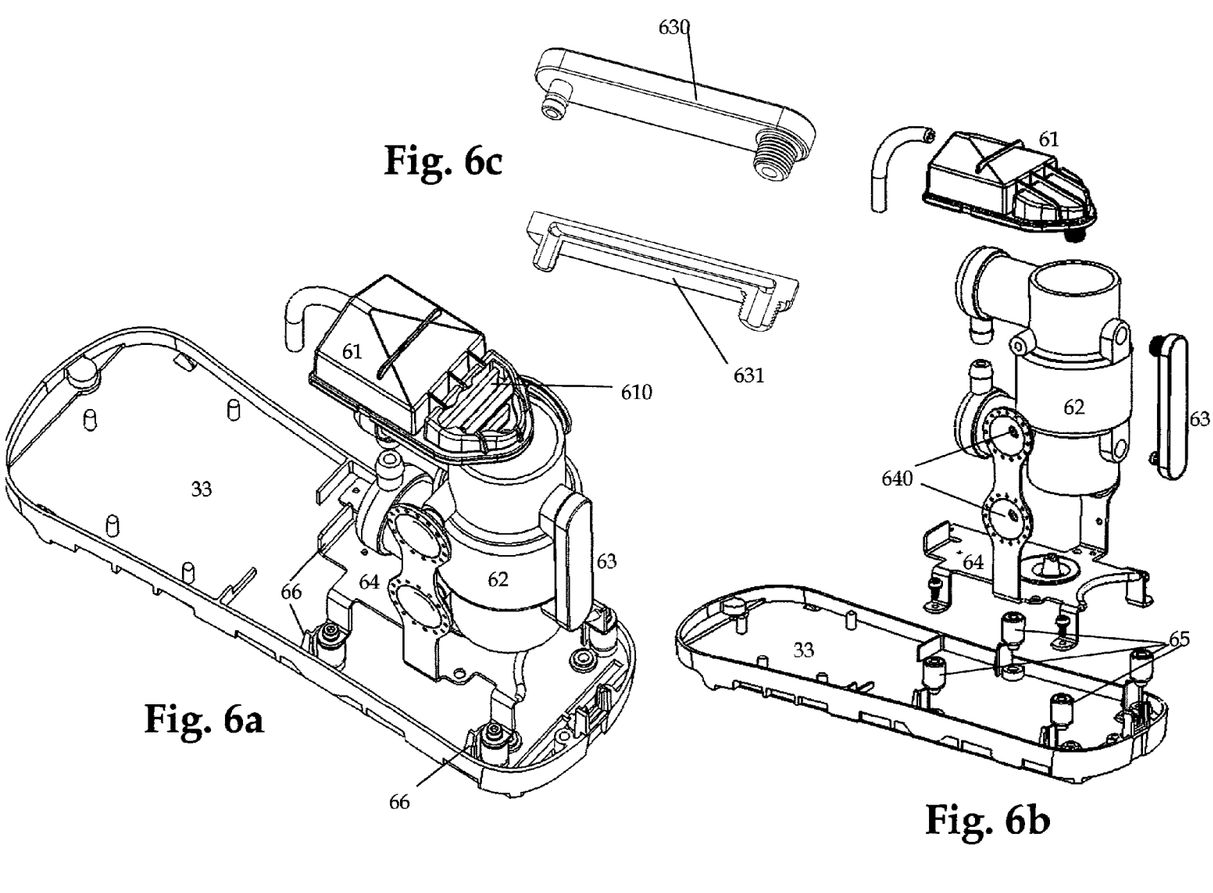
FIG. 6 illustrates the arrangement of the compressor, mounting bracket, air filter and air input member incorporated in the novel concentrator shown in FIG. 2.

Referring to FIGS. 6a, b and c, details of the compressor side of the novel concentrator are shown. In the exemplary version depicted, a compressor bracket 64 is mounted to panel 33. Bracket 64 is preferably mounted to panel 33 with shock/vibration isolating elements which in the exemplary version shown are rubber feet 65. Feet 65 preferably have a durometer between 20 A and 60 A. Compressor 62 is in turn mounted to bracket 64 with another set shock/vibration isolation elements, providing two levels of isolation. In the exemplary version, the second set of isolators is fabricated on the bracket as overmolded rubber 64. Panel 33 in an as-built configuration is the only housing panel with structural mounting for a vibrating component. Panel 33 is an internal panel where the battery is mounted on the underside of the panel. This panel is particularly suited for compressor mounting since the highly mass dense battery absorbs much of the transmitted vibration and prevents the transmission of vibration to the side panels that may contact the user while the device is being carried. In the inventors' prior art concentrator the compressor was mounted to a separate internal chassis that was then surrounded by housing components which led to added weight and size. The separate internal chassis of the prior art concentrator was also more susceptible to damage during drop or impact because the structure was not supported across much of its surface area. Panel 33 is fully supported by battery 22 leading to a much stronger and more resilient design.

Bracket 64 may be made of aluminum for example and in the exemplary version the compressor 62 is a two piston unit. The two piston inputs are connected by low profile compliant member 63. Element 63 in the embodiment shown is a rubber duct 630 and 631 with one snap fit and one threaded attachment to allow for vertical compliance since the compressor assemblies are pressed onto the motor shaft without a hard stop to prevent bearing loading. It may be made from two joined molded rubber pieces and the air channel preferably is between 0.02 and 0.08 sq in. The compliant member preferably has a durometer between 20 A and 70 A to prevent the flat surfaces from resonating noise. The inventors tried multiple materials and fabrication methods and achieved unacceptable results until the proper material durometer were selected. The flat geometry of the compliant member allows for adequate cross section to prevent flow loss from the compressor while also minimizing the protrusion height from the concentrator. With the small external dimensions of a carried portable oxygen concentrator all components must be optimized to reduce space in critical directions. Prior art intake joining tubes were two hard plastic cylinders that slid internal to one another for compliance and protruded as much as twice as far from the compressor as the inventors compliant member 63.

Air filter 61 is preferably arranged with its input and output at right angles and had tortuous air path 610 again for noise isolation. Air filter 61 is plumbed to the air blower with compliant tubing in the durometer range of 20 A to 60 A. The compressor mounting arrangement preferably also includes bump stops 66 to limit compressor deflection in the event of the concentrator being dropped or impacted. Stops 66 are placed adjacent to mounting feet 65 and compressor 62. The stops 66 built into bracket 64 substantially prevent the compressor from colliding with delicate components like the printed circuit board or the external housing components. The bump stops 66 adjacent the mounting feet 65 also allow for softer mounting feet to be used without risk of tearing due to over deflection during drop impact. Bracket 64 may also include mounting for beds with compliant airflow elements.

When assembled, the compressor filter assembly us mounted to the housing through two layers of isolation and only connected to the rest of the system through compliant elements. Thus the assembly is highly resistant to shock and displacement while providing vibration and noise isolation.

Figure 7A:
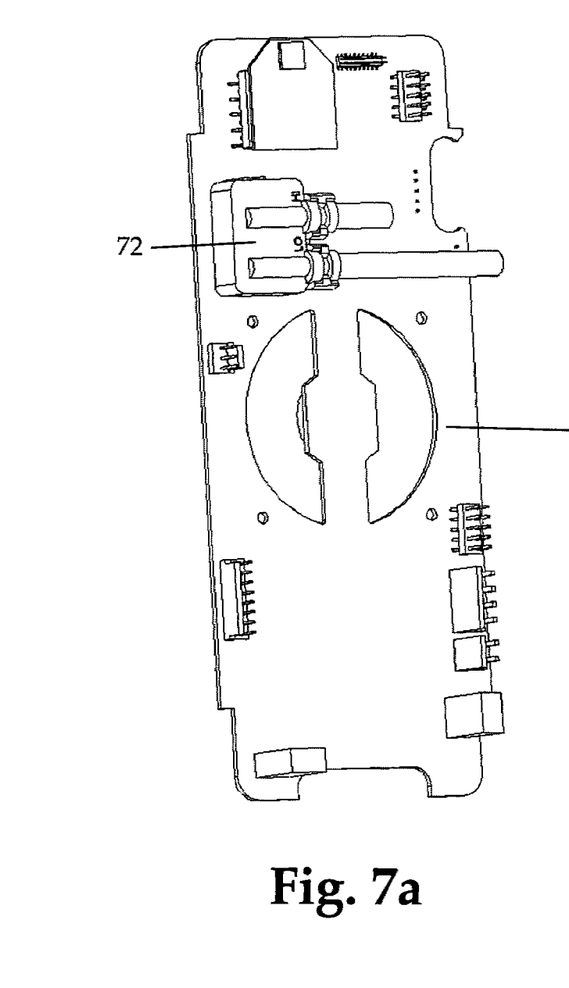
FIG. 7 shows a novel pressure sensor mount incorporated in the novel concentrators shown in FIG. 2.
Figure 7B:
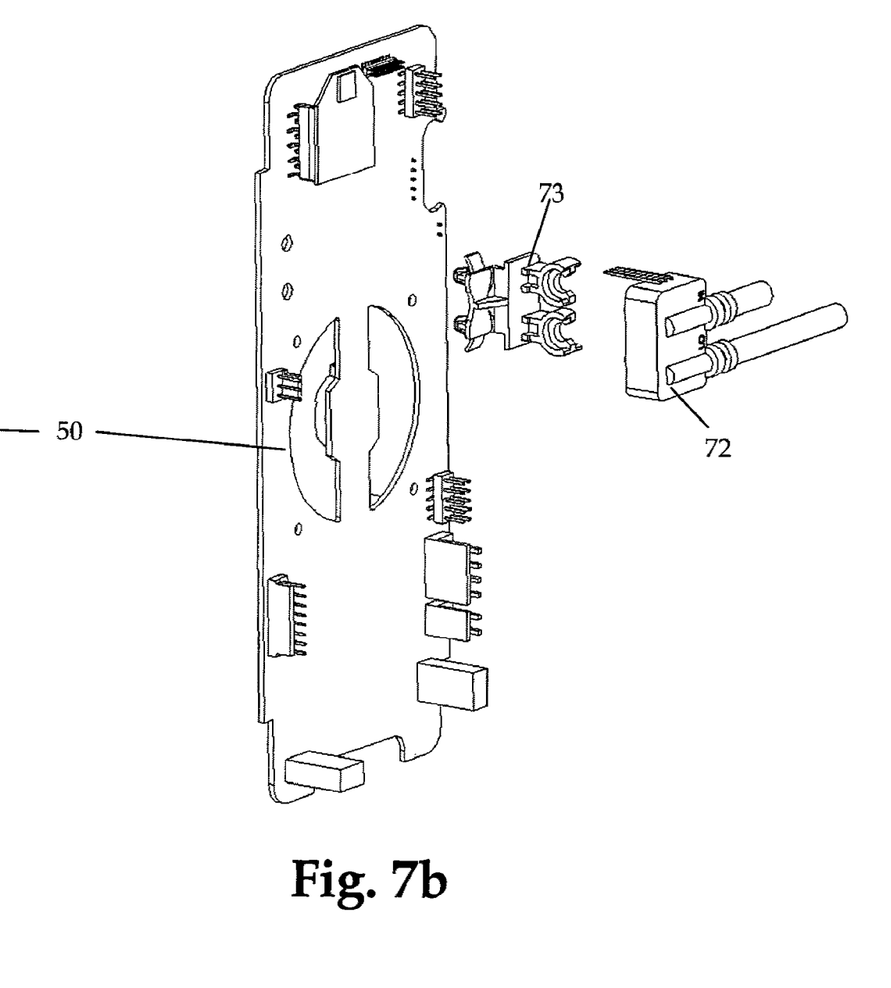

FIGS. 7a and 7b illustrate another embodiment of the novel concentrator. Pressure sensor 72 is designed to mount to a circuit card 50 with two fasteners. The in effect is a stiff fixed mounting that can create a torque or twist on the sensor between the mounting screws and the barbed tubing connections. Due to the shock, vibration and general motion experienced in the portable concentrator environment, this fixed mounting point induced strain can couple vibration into the sensor and can affect the quality of the measured reading. The inventors developed clip 73 which snap mounts to the sensor 72 and is a cantilever designed to mount into fastener points intended for the sensor, while suspending the sensor itself so that it is mounted near the barbed tubing connections to relieve any strain or stress on the body of the sensor where the delicate pressure measuring components are housed. This strain relief in effect greatly diminishes the vibration coupled into the sensor and allows for more reliable and more sensitive breath detection capabilities.

Figure 8:
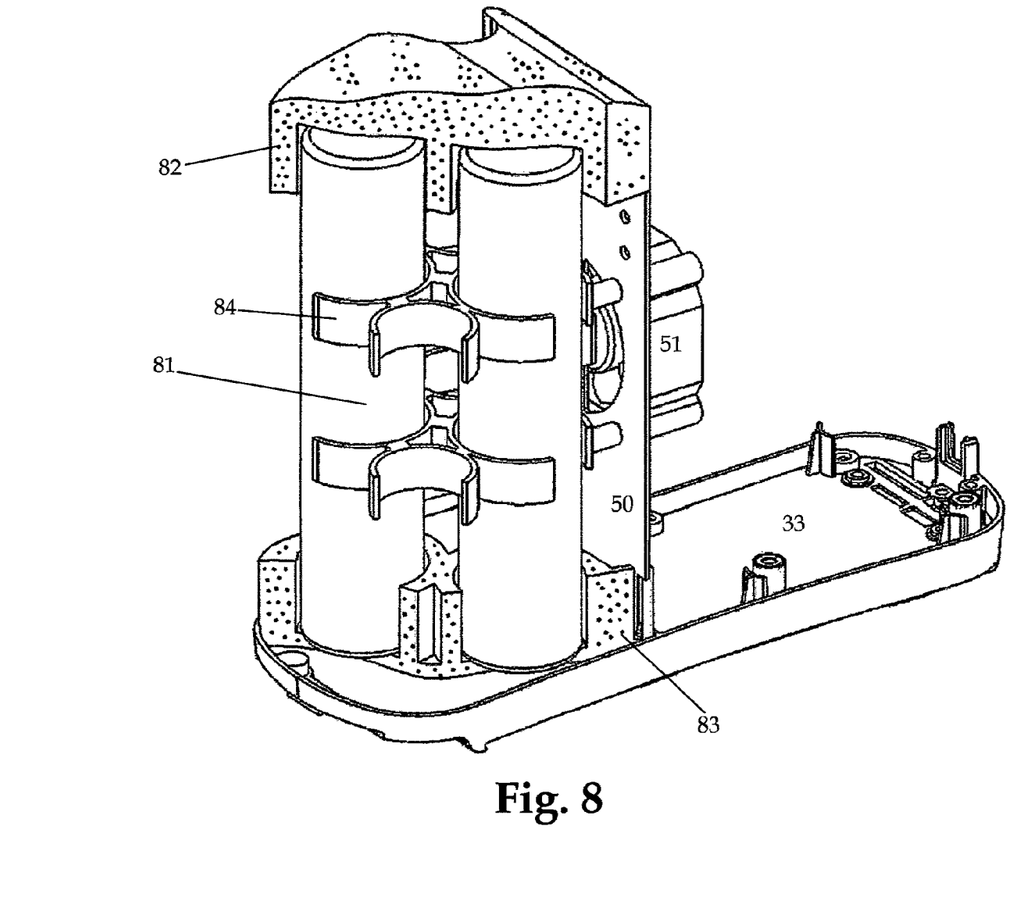
FIG. 8 depicts the isolation and mounting of the adsorbent columns incorporated in the novel concentrator of FIG. 2.

Referring to FIG. 8, the absorber bed side of the concentrator of one embodiment is detailed. Absorber columns 81 are supported, preferably at the top and bottom by isolation elements which fit into the housing panels such as panel 33. These elements are in the exemplary version shown, foam blocks 82 and 83 with cutouts supporting the columns. The columns are located and held relative to each other by clips 84. Clips 84 and blocks 82 and 83 may also carry one or more other items in addition to absorber beds, including air dryers, an oxygen sensor, and product gas accumulator. Thus the columns and other items are floating in the housing with no hard contact to the housing at all. This arrangement greatly improves the durability and survivability of the concentrator while providing yet more noise and vibration isolation. Further in some embodiments, the columns are held in the concentrator without any screws whatsoever allowing for a very comply column replacement of the zeolite is ever contaminated.

Figure 9:
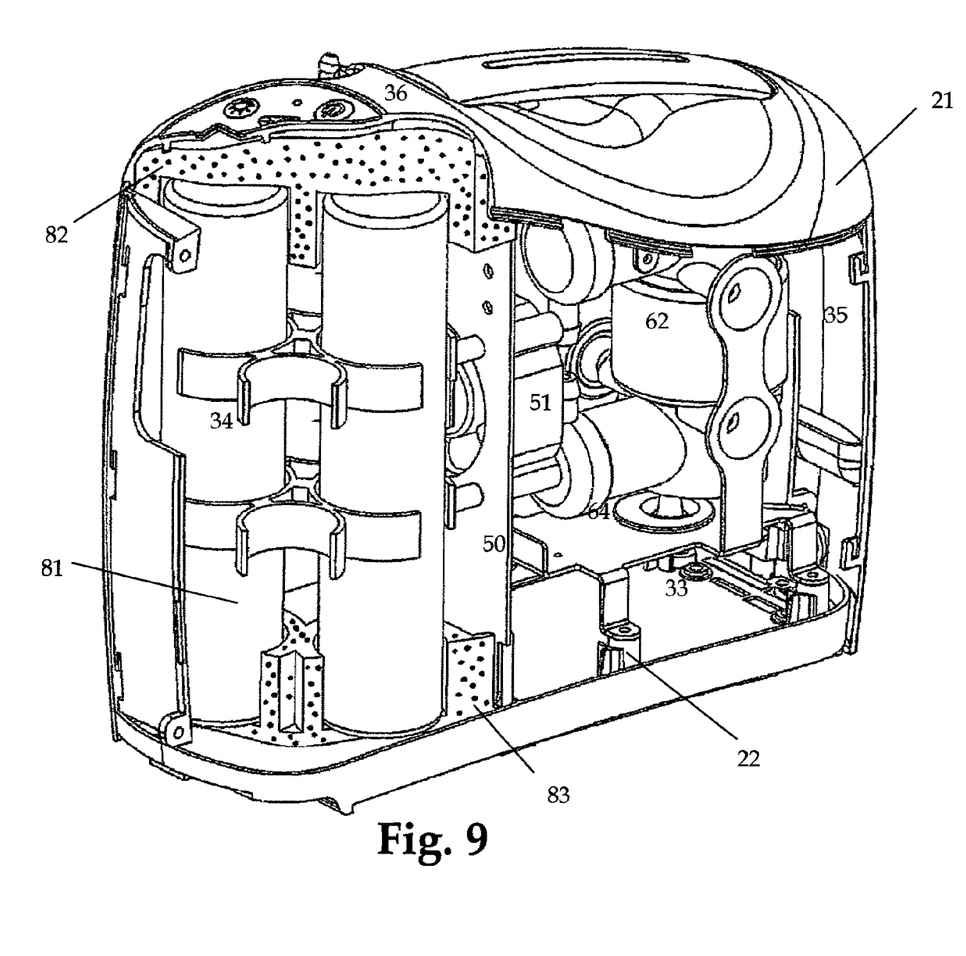
FIG. 9 depicts the novel concentrator of FIG. 2 in a substantially assembled form.

In addition, noise barrier 50 and blower 51 may also be mounted in the foam blocks. The resulting assembly shown in FIG. 9 illustrates the overall concentrator assembly of one embodiment. Rigid and strong shell 21 composed of interlocking panels and locked by battery 22 has no direct contact with any interior components. The columns 81, dryer, accumulator, and all electronics 50 and fan 51 float in a float in a foam chassis 82 and 83 on one side of the air barrier. Compressor 62 vibrates too much to use a foam chassis, so it and all directly attached components are supported by two levels of rubberized isolation, again with no direct hard attachment to the exterior housing panels. In one implementation, the only communication between the two sections is by way of compliant airflow elements such as soft plastic tubing and the like. Airflow is carefully designed to reduce noise. The result is a very hard shell, with all interior components possessing a large amount of freedom of motion relative to the shell and each other, producing an extremely damage resistant and very quiet design.

The foregoing description of the preferred embodiments of the present invention has shown, described and pointed out the fundamental novel features of the invention. It will be understood that various omissions, substitutions, and changes in the form of the detail of the apparatus as illustrated as well as the uses thereof, may be made by those skilled in the art, without departing from the spirit of the invention. Conse-

We claim:

1. A portable oxygen concentrator, comprising:
   At least two absorber columns, At least two vibration/shock isolating column mounting elements; and,
   Removable housing panels including at least three of the front, back, right, left, top and bottom panels, wherein at least two of the panels include a provision for air intake or exhaust; wherein;
   The column mounting elements comprise isolating material blocks with cutouts for ends of the columns thereby suspending the columns in the housing with no direct attachment to the housing or any other part of the concentrator;
   Wherein the concentrator weighs less than 8 pounds, produces less than 45 dba acoustic noise when operating, and has an output gas flow of less than 5 lpm.

2. The concentrator of claim 1 wherein the column mounting elements are foam blocks with appropriate cutouts.

3. The foam of claim 2 comprising of molded urethane foam.

4. The concentrator of claim 1 further comprising clips to locate and retain the columns within the column mounting elements.

5. The concentrator of claim 1 wherein the column mounting elements comprise mounting provision for a circuit board.

6. The circuit board of claim 5 wherein the circuit board mounts an air blower, which may comprise a cooling fan.

7. The concentrator of claim 6 wherein the circuit board is mounted to the column mounting elements disposed as an air barrier between an inlet and an outlet side of the concentrator with fluid communication between the two sides by way of the air blower.

8. The concentrator of claim 4 wherein the column mounting clips additionally mount one or more of an air dryer, oxygen accumulator, or oxygen sensor.

* * * * *